(12) United States Patent
Trebbi et al.

(10) Patent No.: US 9,192,689 B2
(45) Date of Patent: Nov. 24, 2015

(54) LYOPHILIZING OR STERILIZING MACHINE WITH MOVEMENT APPARATUS FOR LOADING PLANES

(71) Applicant: I.M.A. INDUSTRIA MACCHINE AUTOMATICHE SPA, Ozzano Dell'Emilia (IT)

(72) Inventors: Claudio Trebbi, Medicina (IT); Gabriele Gabusi, Castenaso (IT)

(73) Assignee: I.M.A. INDUSTRIA MACCHINE AUTOMATICHE SPA (IT)

( * ) Notice: Subject to any disclaimer, the term of this patent is extended or adjusted under 35 U.S.C. 154(b) by 0 days.

(21) Appl. No.: 14/416,944

(22) PCT Filed: Jul. 23, 2013

(86) PCT No.: PCT/IB2013/001593
§ 371 (c)(1),
(2) Date: Jan. 23, 2015

(87) PCT Pub. No.: WO2014/016659
PCT Pub. Date: Jan. 30, 2014

(65) Prior Publication Data
US 2015/0224215 A1    Aug. 13, 2015

(30) Foreign Application Priority Data
Jul. 23, 2012   (IT) .............................. MI2012A1275

(51) Int. Cl.
*F26B 5/06* (2006.01)
*A61L 2/26* (2006.01)
(52) U.S. Cl.
CPC .... *A61L 2/26* (2013.01); *F26B 5/06* (2013.01)
(58) Field of Classification Search
CPC .................................. F26B 25/08; F26B 5/06
USPC .............................................. 422/300; 34/62
See application file for complete search history.

(56) References Cited

U.S. PATENT DOCUMENTS 3,168,198 A    2/1965  Shelley
8,820,516 B2 * 9/2014  Christ ........................... 198/747

FOREIGN PATENT DOCUMENTS

| EP | 0391208 A1 | 10/1990 |
| EP | 2019277 A2 | 1/2009 |
| WO | 0208092 A1 | 1/2002 |
| WO | 2011045008 A1 | 4/2011 |

OTHER PUBLICATIONS

International Search Report and Written Opinion From PCT/IB2014/0015393, mailed Jan. 30, 2014.

* cited by examiner

*Primary Examiner* — Sean E Conley
(74) *Attorney, Agent, or Firm* — Calfee, Halter & Griswold LLP

(57) ABSTRACT

Lyophilizing or sterilizing machine, comprising a lyophilizing or sterilizing chamber, a plurality of loading planes, having a loading surface disposed inside the chamber and overlapping each other, and a movement apparatus to load on and unload from the loading surface of the loading planes, containers the content of which is to be treated in the chamber. The movement apparatus comprises at least one loading/unloading slider mobile on horizontal guides. The loading planes are associated with vertical movement guides. Each of the loading planes comprises at least two opposite lateral flanks, a plurality of through holes being present on at least one of the lateral flanks in order to house the vertical guides. The through holes define a lateral guide solid with the loading plane, at least one through seating being present between said lateral guide and the loading surface to freely house a respective horizontal guide.

4 Claims, 3 Drawing Sheets

LYOPHILIZING OR STERILIZING MACHINE WITH MOVEMENT APPARATUS FOR LOADING PLANES

CROSS-REFERENCE TO RELATED APPLICATIONS

This application is the U.S. national phase entry of PCT/IB2013/001593, with an international filing date of 23 Jul. 2013, which claims the benefit of Italian Application Serial No. MI2012A001275, with a filing date of 23 Jul. 2012, the entire disclosures of which are fully incorporated herein by reference.

FIELD OF THE INVENTION

The present invention concerns a lyophilizing and/or sterilizing machine comprising loading planes and a movement apparatus for said loading planes.

More precisely, the present invention concerns the guide systems for moving the loading sliders of containers to be loaded onto loading planes inside a lyophilizing or sterilizing machine, and also the systems for moving said planes.

BACKGROUND OF THE INVENTION

Movement apparatuses of the loading planes of lyophilizing and/or sterilizing machines are known.

Hereafter, the reference to lyophilizing machines comprises both lyophilizing and sterilizing machines and combined machines.

The vertical movement of each loading plane inside the chamber occurs using the aid of vertical guides, normally four, two for each side of the plane. The vertical guides are solid with each loading plane and are able to cooperate with suitable protuberances disposed on opposite sides of each loading plane.

The vertical guides, not to be confused with possible anti-oscillation guides disposed outside the planes, connect one plane to the other so that, moving the or an upper loading plane, the plane concerned is also moved vertically.

The vertical guides mainly serve to move the respective loading plane vertically.

Normally, the vertical guides of the various loading planes, usually four for each plane, are disposed adjacent to each other at the sides of all the loading planes.

Each group of vertical guides relating to a loading plane necessarily cooperates with only one specific loading plane. It follows that each loading plane, in the lateral zones, is configured differently from all the others.

This configuration complicates the use of loading sliders or other similar or comparable means, which move the containers from a preparation plane, disposed outside the chamber, to the loading plane and vice versa.

It is known that for said loading sliders it is preferable that suitable horizontal guides are provided which, in the presence of said vertical guides, can either be upended or occupy useful spaces of the loading surface of each loading plane.

Moreover, the lateral bulk created by the vertical guides can limit and/or obstruct the presence of the horizontal guides, whether they are mobile or fixed on the loading plane.

Another disadvantage consists of the different configuration of the loading planes in their zone cooperating with the respective vertical guides. Since each group of vertical guides cooperates with a specific loading plane, this configuration complicates and makes more costly the production steps of the loading plane, as well as the assembly steps in the lyophilizing chamber.

Moreover, the protuberances provided for housing the vertical guides can constitute obstacles, interference or entanglement elements, in which the possible flexible cables moving inside the chamber can become entangled.

One example of a solution in the state of the art is described in WO 2011/045008 A1, which refers to a loading/unloading device for a drying chamber of a dryer.

One purpose of the present invention is to obtain a structure of the loading planes for lyophilizing machines which is identical for all the loading planes, which is simple to make because it is unified, reducing costs, and which guarantees stability to the movement of the loading planes.

Another purpose of the present invention is to obtain a movement apparatus which has a reduced bulk, which guarantees ease of production and assembly in the machine and a low degree of wear of its parts.

Another purpose of the present invention is to obtain horizontal guides for a loading slider, which guides are disposed at the sides of the loading surface of each loading plane, in which said horizontal guides are independent from the loading plane and substantially do not interfere with the useful loading surface.

Another purpose of the present invention is to obtain horizontal guides which allow the loading slider to not interfere with the vertical guides which serve to move the loading planes, positioning said loading planes each time in the desired loading/unloading position.

Another purpose of the present invention is to obtain horizontal guides for the loading slider, or similar means, which are stable and autonomous in solidarity, possibly temporarily, with respect to the loading planes.

The Applicant has devised, tested and embodied the present invention to overcome the shortcomings of the state of the art and to obtain these and other purposes and advantages.

SUMMARY OF THE INVENTION

The present invention is set forth and characterized in the independent claim, while the dependent claims describe other characteristics of the invention or variants to the main inventive idea.

In accordance with the above purposes, a lyophilizing and/or sterilizing machine according to the present invention, which overcomes the limits of the state of the art and eliminates the defects therein, comprises a movement apparatus associated with a treatment chamber, or lyophilizing chamber, of the lyophilizing machine.

A plurality of loading planes able to support containers, the content of which is to be treated, is disposed inside the lyophilizing chamber.

Each loading plane cooperates with specific vertical guides for its vertical movement. If there are four loading planes for example, and if every loading plane is associated with four vertical guides, normally disposed in proximity to its tops, in total, there are, for each side of the loading plane, eight independent vertical guides in twos associated with a specific loading plane.

Externally and in contact with the edges of the loading planes, anti-oscillation guides can be provided which cooperate with all the loading planes, advantageously in all their vertical positions.

The movement apparatus of the containers to be treated comprises at least horizontal guides for the movement of a loading/unloading device, or slider, able to transfer the containers onto the loading planes, from the outside to the inside and vice versa, of the lyophilizing chamber.

The movement apparatus of the present invention allows to use, on the one hand, the same type of loading plane which is uniform and constant for all the loading planes and, on the other hand, provides horizontal guides, autonomous and not interfering with the useful loading surface, along which the loading/unloading device or slider or similar means is made to slide. The horizontal guides are independent of the loading planes, the sliding plane of which is stable and defined or definable as desired.

The loading/unloading device or slider or other suitable mean to load and unload the containers can be driven in many ways, for example with a mechanical motor, an electric motor, a magnetic linear motor, etc.

It is clear that the horizontal guides must be mating to cooperate with the loading and unloading slider.

According to a characteristic feature of the present invention, each of the loading planes comprises, in proximity to at least one of its flanks or lateral edges, at least one through seating through which the horizontal guides pass.

Said seating for the horizontal guides is disposed in an area defined on one side by the limit or lateral flank of the loading surface of the corresponding loading plane and on the other side by the vertical guides of the loading plane.

There is a plurality of through holes aligned and substantially parallel to the lateral edge, in each loading plane and they define the vertical guide mean. The holes are equal in number to the vertical guides which operate at the side of each loading plane. Once in position, the through holes of one loading plane are vertically aligned at least with the through holes of the upper and/or lower loading plane. Each of the through holes of each loading plane is able to house a vertical guide, each loading plane being moved by the respective vertical guides.

According to a variant, the through holes are provided in the loading plane on two or more lines which in practice are parallel to the reference lateral flank.

The at least one through seating, through which the respective horizontal guide transits, is made on each loading plane at the side of the useful loading surface and in proximity to the lateral flank, but internally with respect to the vertical guides and to the holes provided on the loading planes. The horizontal guide is thus able to be anchored, in an adjustable or also stable way, to the internal structure of the lyophilizing chamber, for example in relation to the bottom or to a wall of the chamber.

According to the invention, each loading plane, in the loading or unloading step, is aligned or substantially aligned to the upper end of the horizontal guide. A single loading plane at a time cooperates with the horizontal guide or guides, in the loading and unloading position. The through seatings provided on the sides of the loading planes allow the free vertical movement of the loading planes with respect to the horizontal guides which remain fixed, but without creating obstacles or limitations to the containers which have already been loaded or are to be unloaded, nor to the movement means of the loading slider.

The respective horizontal guide is thus between the loading plane proper, or loading surface, and the vertical guides without interfering either with the useful loading surface or with the holes which position the vertical guides. Thus the loading/unloading slider, or other thrust means which require horizontal guides, located at the side of the useful loading surface, does not interfere with the vertical guides nor with the loading surface.

The invention entails that all the loading planes are identical to each other, with a great advantage in cost, as well as a simplification of the production, storage, assembly and maintenance phases.

According to another characteristic feature of the present invention, the horizontal guides are structurally and/or geometrically defined by the characteristics of the loading/unloading device, or slider, or the means which serve to load and/or unload the containers from the loading planes. Consequently, the through seatings provided at the side of the loading surfaces of the loading planes have a size and shape mating to that of the horizontal guides.

According to another characteristic feature of the present invention, the horizontal guide means are aligned with, or are aligned by, horizontal guide means outside the treatment chamber, allowing the movement of the loading device from the outside to the inside, and vice versa, of the treatment chamber.

BRIEF DESCRIPTION OF THE DRAWINGS

These and other characteristics of the present invention will become apparent from the following description of a form of embodiment, given as a non-restrictive example with reference to the attached drawings wherein.

DETAILED DESCRIPTION OF ONE FORM OF EMBODIMENT

Figure 1:
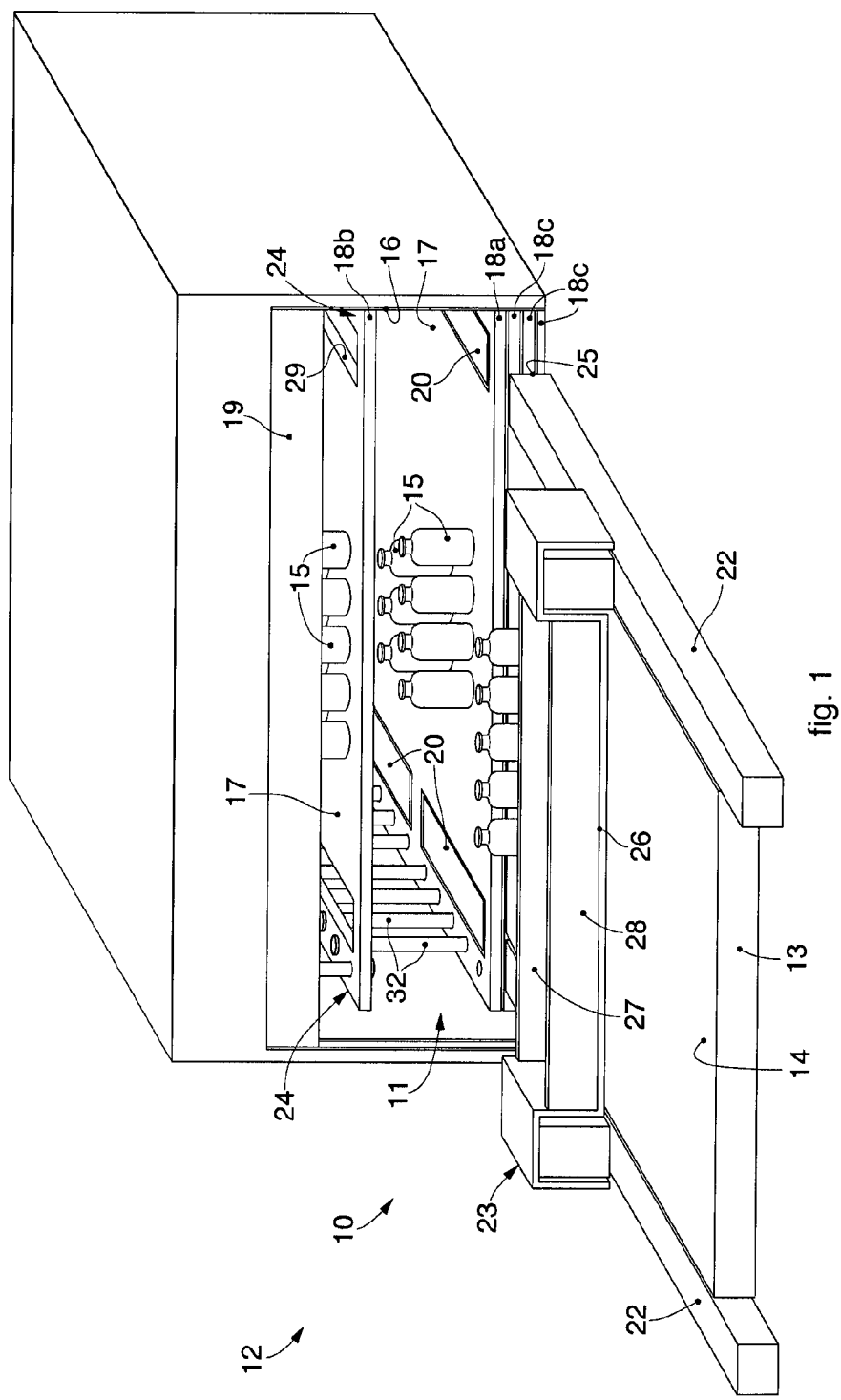
FIG. 1 is a three-dimensional schematic view of a part of a lyophilizing machine in which a movement apparatus according to the present invention is mounted.
Figure 2:
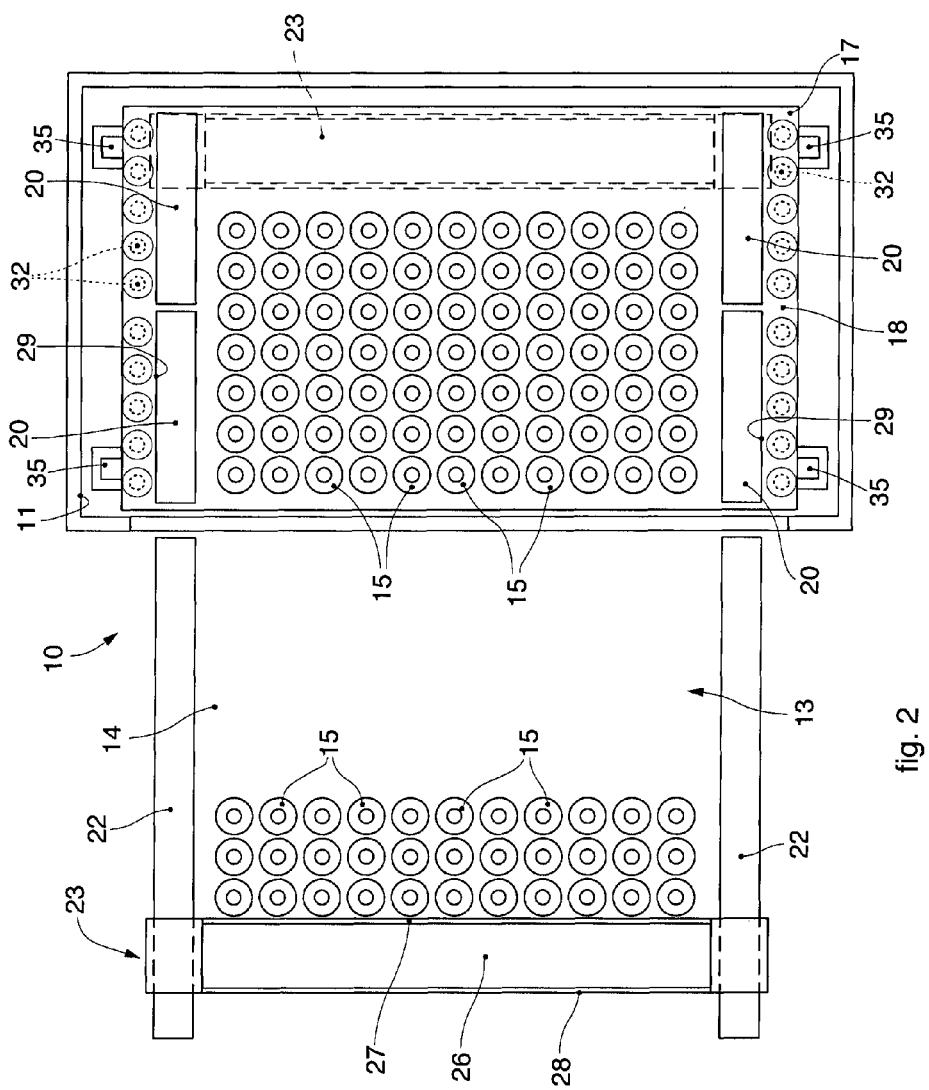
FIG. 2 is a schematic plan view of FIG. 1.

With reference to FIGS. 1 and 2, a movement apparatus 10 according to the present invention is associated with a lyophilizing chamber 11 of a lyophilizing machine 12.

In the drawing a preparation plane 13 can be seen, on the upper surface 14 of which containers 15 are sent or moved, in a known manner, which are prepared there to be sent into the lyophilizing chamber 11 to undergo lyophilization treatment, from which they are then extracted, taken back to the preparation plane 13 and then moved away.

In a known manner, in the loading step the containers 15 are thrust, passing through a loading door 16, from the upper surface 14 of the preparation plane 13 to an upper loading surface 17 of a loading plane 18 of the lyophilizing chamber 11.

The loading plane 18 consists of a loading surface 17, in this case four through seatings 29 and two lateral guides 24, solid with the loading plane 18. By the term lateral guide 24, we mean in this case the combination consisting of five plus five through holes 31, made in proximity to the edges of each loading plane 18, and by corresponding vertical guides 32 which, in this case, are associated in a selective manner with five loading planes 18. There can be continuous anti-oscillation rods 35 at the side of the lateral guides.

The movement apparatus 10, adopted as desired by the constructor, is able to move the containers 15 on the loading surface 17 of each loading plane 18.

During the unloading step, the containers 15 are thrust, passing through the same loading door 16, from the loading surface 17 to the preparation plane 13.

A sealing door 19 is provided to seal the lyophilizing chamber 11.

Figure 3:
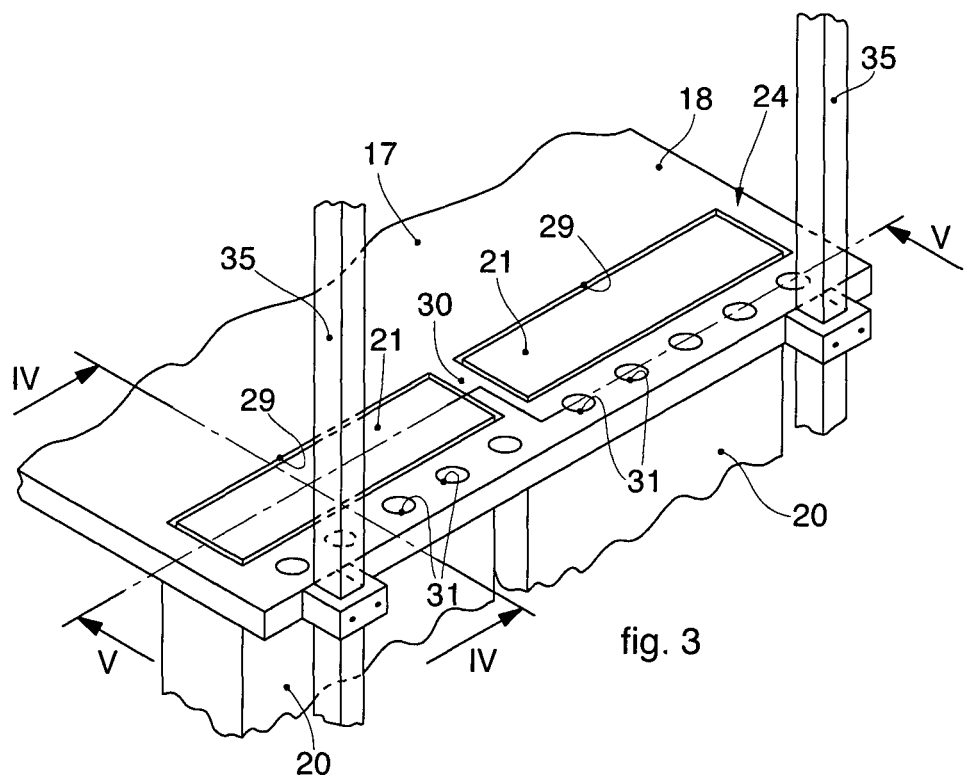
FIG. 3 is a three-dimensional view of a part of the movement apparatus according to the present invention.
Figure 4:
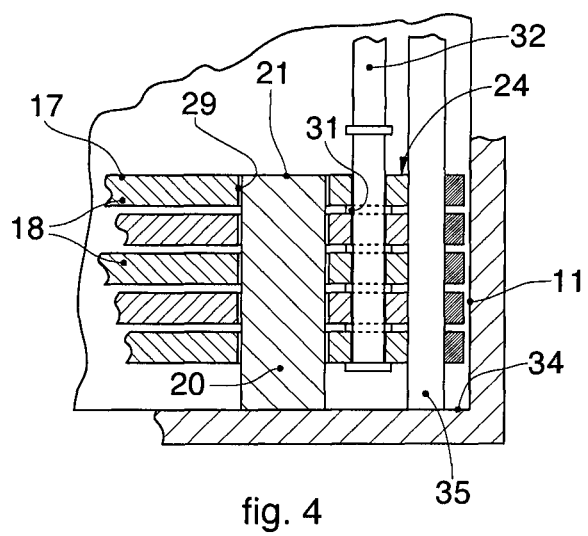
FIG. 4 is a section of FIG. 3 from IV to IV.

In the solution shown in FIGS. 1 and 2, there are, by way of example four, horizontal guides 20 located at the side of the loading surface 17 and cooperating with the through seatings 29. The horizontal guides 20 have an upper surface 21 (FIG. 3), and cooperate with horizontal guides 22 outside the chamber 11.

On the horizontal guides 20 and 22 a loading/unloading slider 23 or other analogous mean moves, in order to carry out the loading and unloading operations of the containers 15. In the case shown here, between the internal horizontal guides 20 and the external horizontal guides 22, by way of example, there are intermediate spaces 25. The intermediate spaces, which during the working step are occupied in a known manner, allow the sealing door 19 to close the loading door 16.

In this case, by way of example, the loading/unloading slider 23 comprises a bearing structure consisting of a base 26, possibly mobile vertically, and in this case two thrust walls, respectively a front vertical wall 27, able to thrust the containers 15 into the lyophilizing chamber 11, and a rear vertical wall 28, able to remove the containers 15 from the lyophilizing chamber 11. The thrust means for the containers 15 can be of any type.

In the example shown here, since five loading planes 18 are provided, each loading plane 18 comprises on each respective flank five plus five through holes 31. This in the case where every loading plane 18 cooperates with four vertical guides, respectively two for each lateral flank.

Furthermore, in the example shown (FIG. 3), in cooperation with each flank of the loading surface 17, there are through seatings 29, for example rectangular, in this case shown two for every side. The through seatings 29 are able to define the compartments in which the horizontal guides 20 are freely housed. More precisely, the through seatings 29 allow the loading planes 18a-18e to move vertically with respect to the horizontal guides 20. The horizontal guides 20 can be attached to the floor or anchored for example to the structure of the chamber 11, so as to position their upper surface 21 always aligned and always in the same position.

There can be one or more horizontal guides 20 for every flank of the loading plane 18.

The loading position of the loading surface 17 cooperates with the upper surface 21 of the internal horizontal guide 20 so that the loading/unloading slider 23 can perform its function.

The upper surface 21 can be fixed or adjustable in height.

In the case shown here (FIG. 3), the two through seatings 29 cooperate with intermediate connection zones 30 between the loading surface 17 and the lateral guide 24, in which there are the through holes 31.

Inside each through hole 31 a vertical guide 32 is housed.

Each vertical guide 32 cooperates with specific loading planes 18.

According to the configuration of the present invention, therefore, the horizontal guides 20 are between the lateral flank of the loading surface 17 and the lateral guides 24 comprising the vertical guides 32.

This configuration allows the free movement of the loading/unloading slider 23, or other analogous mean, along the internal horizontal guides 20, without any problems of interference with the vertical guides 32.

Another advantage of this configuration is that all the loading planes 18 are identical to each other, thus entailing easy construction, easy storage, easy assembly and easy maintenance thereof.

It is clear that modifications and/or additions of parts may be made to the movement apparatus 10 as described heretofore, without departing from the field and scope of the present invention.

It is also clear that, although the present invention has been described with reference to some specific examples, a person of skill in the art shall certainly be able to achieve many other equivalent forms of movement apparatus, having the characteristics as set forth in the claims and hence all coming within the field of protection defined thereby.

The invention claimed is:

1. A lyophilizing/sterilizing apparatus, comprising:
   a lyophilizing/sterilizing chamber;
   a plurality of loading planes, said loading planes comprises at least two opposing lateral flanks with at least one of said lateral flanks having a plurality of through holes and a loading surface for container of content to be treated wherein said loading planes are disposed inside said chamber and each loading plane overlaps at least one other loading plane;
   at least one vertical guide for movement of the loading planes and in communication with said lateral flanks having a plurality of through holes;
   a movement apparatus having at least one loading/unloading slider disposed on horizontal guides, wherein said horizontal guides comprise a first set of horizontal guides located outside said chamber and a second set of horizontal guides inside said chamber;
   at least one lateral guide in communication with a loading plane, wherein at least one through hole forms a seating with a shape and size freely house a horizontal guide; and
   wherein each of said loading planes has a loading position for direct cooperation with an upper surface of said horizontal guide so that the loading/unloading slider operates on the loading surface.

2. The lyophilizing/sterilizing apparatus of claim 1 wherein horizontal guide passes through all of said loading planes when they are unloaded, and is solid with an internal part of the lyophilizing chamber.

3. The lyophilizing/sterilizing apparatus of claim 2 wherein said upper surface of the internal horizontal guides has a fixed position.

4. The lyophilizing/sterilizing apparatus of 2 wherein said upper surface of the horizontal guides has an adjustable position at least in height.

* * * * *